United States Patent [19]

Baker

[11] 4,048,432

[45] Sept. 13, 1977

[54] 9-(3,5-DI-O-ACYL-β-D-ARABINOFURANOSYL)ADENINE COMPOUNDS AND METHOD FOR THEIR PRODUCTION

[75] Inventor: David Clarkston Baker, Ann Arbor, Mich.

[73] Assignee: Parke, Davis & Company, Detroit, Mich.

[21] Appl. No.: 687,270

[22] Filed: May 17, 1976

[51] Int. Cl.$^2$ .............................................. C07H 19/18
[52] U.S. Cl. ...................................... 536/26; 424/180; 536/24
[58] Field of Search ....................... 536/23, 26, 27, 24

[56] References Cited

U.S. PATENT DOCUMENTS

| | | | |
|---|---|---|---|
| 3,309,358 | 3/1967 | Hanze | 536/27 |
| 3,354,160 | 11/1967 | Duschinsky et al. | 536/23 |
| 3,457,253 | 7/1969 | Wechter | 536/27 |
| 3,651,045 | 3/1972 | Haskell et al. | 536/26 |

Primary Examiner—Johnnie R. Brown
Attorney, Agent, or Firm—David B. Ehrlinger; Stephen Raines; Frank S. Chow

[57] ABSTRACT 9-(3,5-Di-O-acyl-β-D-arabinofuranosyl)adenine compounds and their production by reacting in each case a 9-(5-O-tri-substituted-silyl-2,3-di-O-acyl-β-D-arabinofuranosyl)adenine compound with a tetraalkylammonium fluoride. The compounds are useful as antiviral agents. The compounds are stable and being lipophilic are adaptable to long-acting and depot injectable pharmaceutical formulation.

8 Claims, No Drawings

9-(3,5-DI-O-ACYL-β-D-ARABINOFURANOSYL-)ADENINE COMPOUNDS AND METHOD FOR THEIR PRODUCTION

SUMMARY AND DETAILED DESCRIPTION

The present invention relates to new organic compounds that are useful as pharmacological agents and to a method for their production. More particularly, the invention relates to new 9-(3,5-di-O-acyl-β-D-arabinofuranosyl)- adenine compounds that are represented by the formula

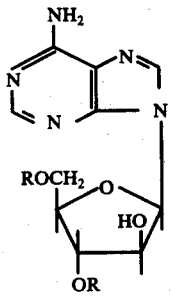

I where R is a straight or branched chain alkanoyl group having from 2 to 4 carbon atoms. Examples of alkanoyl groups represented by R are acetyl, propionyl, butyryl, and isobutyryl.

In accordance with the invention, 9-(3,5-di-O-acyl-β-D-arabinofuranosyl)adenine compounds having formula I are produced by reacting a 5-silyl ether derivative represented by the formula

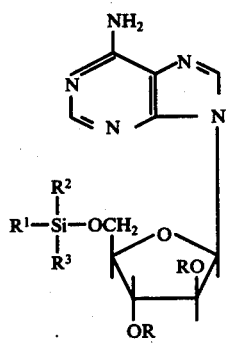

II with an equivalent quantity of a tetra(lower)alkylammonium fluoride where R has the same significance, $R^1$ is lower alkyl, and $R^2$ and $R^3$ represent lower alkyl, phenyl or together are tetramethylene. The term "lower alkyl" as used herein refers to a 1 to 4 carbon alkyl group. The choice of the silyl group of the starting material is not critical, since the group is removed during the reaction and is replaced when the acyl groups rearrange from the 2,3-positions to the 3,5-positions. Examples of such silyl groups for purposes of the invention are trimethylsilyl, triisopropylsilyl, diisopropylmethylsilyl, tert-butyldiphenylsilyl, isopropyltetramethylenesilyl, and tertbutyltetramethylenesilyl. For purposes of the invention any tetraalkylammonium fluoride which is soluble in the organic solvent used is suitable. A preferred reagent is tetrabutylammonium fluoride. The use of materials in the reaction which prevent acyl group rearrangement (such as alkanoic acids, for example) is avoided. The reaction is advantageously carried out in an organic ether solvent medium. Suitable solvents for this purpose include tetrahydrofuran, dioxane, 1,2-dimethoxyethane, diethylene glycol dimethyl ether, and mixtures of these which dissolve the tetraalkylammonium fluoride used in the reaction. The precise temperature and duration of the reaction are not critical and may be varied widely depending upon the reactants and solvent employed. Suitably, the reaction temperature can be varied between about 0° and about 50° C. for 15 minutes to 10 hours, with the longer times being used at the lower temperatures. Preferred conditions are temperatures from 20° to 30° C. for 1 to 3 hours. Although one equivalent of tetraalkylammonium fluoride is needed per mole of silyl ether, it is preferred to use 2 to 4 equivalents.

The 9-(3,5-di-O-acyl-β-D-arabinofuranosyl)adenine compounds are new chemical compounds that are useful as pharmacological agents, especially as antiviral agents against herpes virus.

Their activity as antiviral agents can be quantitatively measured in an in vitro test by utilizing the plaque reduction technique first developed by Dulbecco (*Proc. Natl. Acad. Sci.*, Volume 38, pages 747-752) and modified by Hsiung and Melnick (*Virology*, Volume 1, pages 533-535). In this test, a complete cell monolayer is first grown on a glass test unit. The growth medium is then removed, and the virus is adsorbed on the cell monolayer for a measured time period. In the absence of an antiviral agent, the virus will destroy well-defined areas of cells, called plaques, that can be seen macroscopically when the vital stain, neutral red, is added to the system. To test the inhibiting effect of a given compound, the test compound in solution is added to the virus-cell system, and the whole is covered with a nutrient agar overlay containing neutral red. After incubation, the plaques are counted, and the number of plaques produced in the system containing the test compound is compared with the number produced in the control systems, from which only the test compound is omitted. The inhibitory activity of a test compound is reported as the percentage reduction of the plaque count on the test units compared with that on the controls.

When tested by this plaque reduction technique, with 4 oz. glass bottles serving as the test units and H. Ep. No. 2 cells making up the cell monolayer, compounds of the invention, at a concentration ranging from about 7 to 70 micrograms/ml. in Hank's Balanced Salt Solution (pH 7-8), typically were found to give complete or substantially complete plaque reduction against herpes simplex.

The compounds of the invention are structurally related to 9-(β-D-arabinofuranosyl)adenine, which is known to be an antiviral agent that is active against herpes virus. The latter compound has been reported to be more active in vitro against herpes virus than its 5'-benzoyl ester whereas its 5'-palmitate ester was inactive in the same test (Renis et al., *J. Med. Chem.*, 16, 754); its 5'-formate ester has been reported (Repta et al., *J. Pharm. Sci.*, 64, 392) to be unstable in aqueous solution. Other known esters of 9-(β-D- arabinofuranosyl)adenine are the 2',3',5'-triesters (described in U.S. Pat. No. 3,651,045) which are more efficiently absorbed upon oral administration than 9-(β-D-arabinofuranosyl)- adenine. The compounds of the invention are unique in that they not only exhibit good antiviral activity but are stable in aqueous solution and also have outstanding lipophilic properties which make the compounds adaptable to a wide variety of oral, topical and parenteral pharmaceutical formulations, including long-acting and depot injectable formulations. Preferred compounds of the invention for their antiviral activity, water solubility and/or lipophilicity are 9-(3,5-di-O-propionyl-β-D-arabinofuranosyl) adenine and 9-(3,5-di-O-isobutyryl-β-D-arabinofuranosyl) adenine.

The invention is illustrated by the following examples.

EXAMPLE 1 a. To a well-stirred solution of 15.0 g. of 9-[5-O-(tert-butyldimethylsilyl)-β-D-arabinofuranosyl]adenine in 100 ml. of dry pyridine is added 11.1 ml. of propionic anhydride. The solution is stirred at room temperature for 16 hours, treated with 100 g. of crushed ice and stirred one additional hour. The resulting solution is evaporated at reduced pressure at 45° C. and the residue is dissolved in 250 ml. of chloroform. The chloroform solution is washed in turn with aqueous sodium bicarbonate and with water, and is then dried and evaporated to give the product, 9-[2,3-di-O-propionyl-5-O-(tert-butyldimethylsilyl)-β-D- arabinofuranosyl]adenine, suitable for use in the following procedure without further purification.

b. The product obtained by the procedure of paragraph 1 (a) is dissolved in 200 ml. of tetrahydrofuran, the solution is treated with 31.3 ml. of tetrabutylammonium fluoride and allowed to stand at room temperature for 2 hours. The solution is then passed over a 5 × 10 cm. column of dry silica gel. The column is eluted with one liter of tetrahydrofuran and the eluate is evaporated at reduced pressure to give the desired product, 9-(3,5-di-O-propionyl-β-D-arabinofuranosyl)adenine; $[\alpha]_D^{23} = +8.1°$ (C = 1% in chloroform), $\lambda_{max}^{CH_3OH} = 259$ nm ($\epsilon = 14,950$).

c. By substituting 9.5 ml. of acetic anhydride for the propionic anhydride in paragraph 1 (a) and using 200 ml. of dry pyridine, the product obtained by the procedure of paragraph 1 a) is 9-(2,3-di-O-acetyl-5O-(tert-butyldimethylsily)-β-D-arabinofuranosyl)adenine, which, on reaction with 31.3 g. of tetrabutylammonium fluoride in 300 ml. of tetrahydrofuran, following the procedure of paragraph 1 (b), gives 9-(3,5-di-O-acetyl-β-D-arabinofuranosyl)adenine. By substituting 23.4 ml. of butyryl chloride for the propionic anhydride in paragraph 1 (a) and using 17.9 g. of the silyl ether in 250 ml. of pyridine, the product obtained is 9-(2,3-di-O-butyryl-5-O-(tert-butyldimethylsilyl)-β-D-arabinofuranosyl) adenine, which on reaction with 37 g. of tetrabutylammonium fluoride in 350 ml. of tetrahydrofuran following the procedure of paragraph 1 (b) gives 9-(3,5-di-O-butyryl-β-D-arabinofuranosyl)adenine.

EXAMPLE 2 a. To a well-stirred solution of 1.79 g. of 9-[5-O-(tert-butyldimethylsilyl)-β-D-arabinofuranosyl]-adenine in 50 ml. of dry pyridine is added 2.34 ml. of isobutyryl chloride. The solution is stirred at room temperature for 16 hours, treated with 100 g. of chipped ice and stirred one additional hour. The resulting solution is evaporated at reduced pressure at 45° C. and the residue is dissolved in 250 ml. of chloroform. The chloroform solution is washed with aqueous sodium bicarbonate and with water, and is dried and evaporated. The residual product, 9-[2,3-di-O-isobutyryl-5-O-(tert-butyldimethylsilyl)-β-D-arabinofuranosyl]adenine, is suitable for use as a starting material for the procedure of paragraph 2 (b) without further purification.

b. The product of 2 (a) is dissolved in 100 ml. of tetrahydrofuran, the solution is treated with 3.7 g. of tetrabutylammonium fluoride and allowed to stand at room temperature for 2 hours. The solution is then passed over a 5' × 10 cm. column of dry silica gel. The column is eluted with one liter of tetrahydrofuran and the eluate is evaporated at reduced pressure to give the product 9-(2,3-di-O-isobutyryl-β-D-arabinofuranosyl) adenine; m.p. 217.5°–218.5° C. after crystallization from acetone-methanol, $\lambda_{max}^{CH_3OH}$ - 259 nm ($\epsilon = 15,500$).

Preparation of Silyl Ether Starting Materials

The unesterfied silyl ether starting materials specified above are new compounds. These compounds can be prepared from known materials by the following illustrative procedure which provides a tert-butyldimethylsilyl ether.

a. To a well-stirred suspension of 26.7 g. of 9-β-D-arabinofuranosyladenine in 500 ml. of dry dimethylformamide, containing 16.3 g. of imidazole, is added 18.1 g. of tert-butylchlorodimethylsilane. The mixture is stirred, with protection from moisture, for 20 hours at room temperature, then evaporated at reduced pressure at 50°–60° C. The residue is dissolved in 300 ml. of ethyl acetate and the solution is washed with water, dried and evaporated at reduced pressure. The residual syrup is dissolved in 240 ml. of hot chloroform; the solution is diluted to cloudiness with hexane and cooled to crystalline 9-[5-O-(tert-butyldimethylsilyl)-β-D-arabinofuranosyl]adenine, which is collected by filtration, washed with hexane and dried at 80° C. at reduced pressure; m.p. 157°–158° C., $[\alpha]_D^{23} = +4.1°$; $\lambda_{max}^{CH_3OH} = 259$ nm ($\epsilon = 15,000$).

b. By the same precedure of paragraph (a), but by replacing the trialkylchlorosilane with an equivalent quantity of a different chlorosilane (where $R^1$, $R^2$ and $R^3$ have the above-defined significance), one can obtain the corresponding 9-[5-O-($R^1$, $R^2$, $R^3$-substituted)silyl)-β-D-arabinofuranosyl]adenine, for example, one of the following:

9-[5-O-(trimethylsilyl)-β-D-arabinofuranosyl]adenine
9-[5-O-(trisopropylsilyl)-arabinofuranosyl]adenine
9-[5-O-(diisopropylmethylsilyl)-arabinofuranosyl]-adenine
9-[5-O-(tert-butyldiphenylsilyl)-arabinofuranosyl]-adenine
9-[5-O-(isopropyltetramethylenesilyl)-arabinofuranosyl]adenine
9-[5-O-(tert-butyltetramethylenesilyl)-arabinofuranosyl]adenine Any of the mentioned 9-[5-O-($R^1$, $R^2$, $R^3$-substituted)-silyl)-β-D-arabinofuranosyl]adenine compounds can be used as a starting material for the procedure of Example 1 or Example 2 in place of the tert-butyldimethylsilyl ether starting material.

I claim:
1. 9-(3,5-Di-O-acyl-β-D-arabinofuranosyl)adenine compounds having the formula

-continued

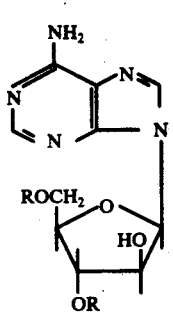

where R is an alkanoyl group having from 2 to 4 carbon atoms.

2. A compound according to claim 1 which is 9-(3,5-di-O-propionyl-β-D-arabinofuranosyl)adenine.

3. A compound according to claim 1 which is 9-(3,5-di-O-isobutyryl-β-D-arabinofuranosyl)adenine.

4. A compound according to claim 1 which is 9-(3,5-di-O-acetyl-βD-arabinofuranosyl)adenine.

5. A compound according to claim 1 which is 9-(3,5-di-O-butyryl-β-D-arabinofuranosyl)adenine.

6. Method for the production of 9-(3,5-di-O-acyl-β-D-arabinofuranosyl)adenine compounds having the formula

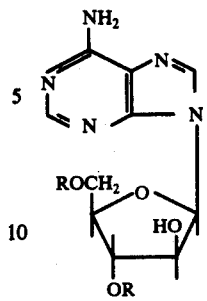

I

-continued where R is an alkanoyl group having from 2 to 4 carbon atoms, which comprises reacting a 5-silyl ether derivative represented by the formula

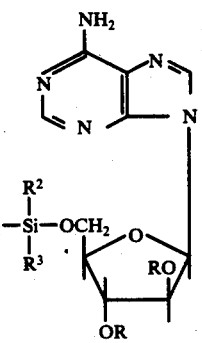

II with an equivalent quantity of a tetra(lower)alkylammonium fluoride where R is an alkanoyl group having from 2 to 4 carbon atoms, $R^1$ is lower alkyl, and $R^2$ and $R^3$ represent lower alkyl or phenyl or together are tetramethylene.

7. Method according to claim 6 where the reaction is carried out at temperatures between about 0° and about 50° C. in an organic ether solvent.

8. Method according to claim 6 where the reaction is carried out with 2 to 4 equivalents of tetraalkylammonium fluoride for each equivalent of silyl ether derivative used.

* * * * *